US 6,566,313 B1

(12) United States Patent
Hohenstein et al.

(10) Patent No.: US 6,566,313 B1
(45) Date of Patent: May 20, 2003

(54) SHAMPOO AND BODY WASH COMPOSITION AND METHOD OF USE THEREOF

(75) Inventors: Karen A. Hohenstein, Los Angeles, CA (US); George Andrassy, Walnut, CA (US)

(73) Assignee: Henkel Corporation, Gulph Mills, PA (US)

( * ) Notice: Subject to any disclaimer, the term of this patent is extended or adjusted under 35 U.S.C. 154(b) by 14 days.

(21) Appl. No.: 09/954,834

(22) Filed: Sep. 17, 2001

Related U.S. Application Data

(60) Provisional application No. 60/233,208, filed on Sep. 15, 2000.

(51) Int. Cl.$^7$ .............................. C11D 1/02; C11D 1/34; C11D 3/30; C11D 3/32; C11D 3/06
(52) U.S. Cl. .................. 510/125; 510/127; 510/137; 510/138; 510/158; 510/159; 510/467; 510/501
(58) Field of Search .................... 510/125, 127, 510/137, 138, 158, 159, 467, 501; 424/70.22, 70.24, 70.27

(56) References Cited

U.S. PATENT DOCUMENTS

| | | |
|---|---|---|
| 3,990,991 A | 11/1976 | Gerstein |
| 4,298,494 A | 11/1981 | Parslow et al. |
| 4,321,156 A | 3/1982 | Bushman |
| 4,321,256 A | 3/1982 | Hasegawa et al. |
| 4,479,893 A | 10/1984 | Hirota et al. |
| 4,701,322 A | 10/1987 | Dixon et al. |
| 4,722,837 A | 2/1988 | Cameron |
| 4,726,945 A | 2/1988 | Patel et al. |
| 4,728,457 A | 3/1988 | Fieler et al. |
| 4,741,855 A | 5/1988 | Grote et al. |
| 4,906,460 A | 3/1990 | Kim et al. |
| 4,938,953 A | 7/1990 | Pena et al. |
| 5,059,414 A | 10/1991 | Dallal et al. |
| 5,077,041 A | 12/1991 | Yamashina et al. |
| 5,078,990 A | 1/1992 | Martin et al. |
| 5,091,171 A | 2/1992 | Yu et al. |
| 5,120,531 A | 6/1992 | Wells et al. |
| 5,137,715 A | 8/1992 | Hoshowski et al. |
| 5,145,607 A | 9/1992 | Rich |
| 5,217,711 A | 6/1993 | De Oliveira |
| 5,227,156 A | 7/1993 | Wiese |
| 5,328,685 A | 7/1994 | Janchitraponvej et al. |
| 5,334,325 A | 8/1994 | Chaussee |
| 5,346,639 A | 9/1994 | Hatfield |
| 5,384,114 A | 1/1995 | Dowell et al. |
| 5,393,519 A | 2/1995 | Dowell et al. |
| 5,456,863 A | 10/1995 | Bergmann |
| 5,556,615 A | 9/1996 | Janchitraponvej et al. |
| 5,562,898 A | 10/1996 | Dowell et al. |
| 5,565,216 A | 10/1996 | Cowsar et al. |
| 5,578,560 A | 11/1996 | Giesen et al. |
| 5,587,154 A | 12/1996 | Dowell et al. |
| 5,610,187 A | 3/1997 | Manning et al. |
| 5,618,522 A | 4/1997 | Kaleta et al. |
| 5,658,558 A | 8/1997 | Schwartz |
| 5,665,267 A | 9/1997 | Dowell et al. |
| 5,683,683 A | 11/1997 | Scafidi |
| 5,783,200 A | 7/1998 | Motley et al. |
| 5,883,068 A | 3/1999 | Hensen et al. |
| 5,925,615 A | 7/1999 | Kern et al. |
| 5,945,093 A | 8/1999 | Duvel |
| 5,955,066 A | 9/1999 | Sako et al. |
| 5,977,038 A | 11/1999 | Birtwistle et al. |
| 6,010,689 A | 1/2000 | Matsumoto et al. |
| 6,015,574 A | 1/2000 | Cannell et al. |
| 6,228,352 B1 | 5/2001 | Leet |

*Primary Examiner*—Gregory DelCotto
(74) *Attorney, Agent, or Firm*—Stephen D. Harper; Gregory M. Hil

(57) ABSTRACT

The present invention provides a conditioning shampoo and/or body wash composition and a method of using the same. The composition of the present invention contains at least one anionic surfactant, at least one conditioning complex, and water. The conditioning complex is formed from at least one tertiary alkyl amidoamine and at least one phosphate ester.

11 Claims, No Drawings

SHAMPOO AND BODY WASH COMPOSITION AND METHOD OF USE THEREOF

CROSS REFERENCE TO RELATED APPLICATIONS

This application claims the benefit under 35 U.S.C. §119 (e) to U.S. provisional application Serial No. 60/233,208 filed on Sep. 15, 2000, the disclosure of which is hereby incorporated by reference in its entirety.

FIELD OF INVENTION

The present invention relates to a shampoo and/or body wash composition and to a method of use thereof. The shampoo or body wash composition is preferably used to both cleanse and condition skin and/or hair treated with the composition. The composition of the present invention contains a conditioning complex that is compatible with anionic surfactants and is substantive to skin and/or hair.

BACKGROUND OF THE INVENTION

Shampoos for cleansing the hair, and body wash compositions for cleaning the skin are commonly formulated with anionic surfactants that produce copious amounts of foam and clean the hair and skin of excess sebum and dirt. However, the anionic surfactants also remove the natural protective oils from the skin and hair, leaving the skin and hair dry and/or rough. Typically, a subsequent separate treatment with a conditioning composition is needed to return the skin and hair to an aesthetically desired state. Investigators have sought to develop shampoo and body wash compositions that both cleanse the skin and hair, and leave the skin and hair soft and moisturized.

For example, much research has been directed to the use of cationic fatty quaternary compounds and/or silicone based compounds as conditioning compounds in shampoos and body wash compositions. Many patents have been issued in this area, including U.S. Pat. Nos. 4,741,855; 5,456,863; 3,990,991; and 5,683,683. Some drawbacks of these compositions include lack of stability, the appearance which is usually opaque, and the rheology which tends to be viscous. Another disadvantage is that these compositions tend to have poor rinseablity from the skin and hair, leading to a greasy, coated feel to the hair or skin.

U.S. Pat. No. 5,945,093 to Duvel discloses a conditioning shampoo composition containing an anionic surfactant, a cationic surfactant, a silicone conditioning agent and a polymeric suspending agent. The cationic surfactant is preferably an acid neutralized amidoamine, that is also disclosed as providing some conditioning properties. A disadvantage of this formulation is that when the amidoamine is neutralized with the acids disclosed therein, the resultant quaternary salt is not substantive to skin and hair, and is easily rinsed, leaving little or no residual softness and/or smoothness.

The present invention provides a shampoo and/or body wash composition which contains a conditioning complex that is strongly substantive to the skin and hair, and does not leave a greasy feel to the skin or hair. The composition can also preferably be formulated to be visually transparent. The conditioning complex also permits the composition to be formulated to the intrinsic pH of healthy skin and hair, which provides the treated skin and hair with a cosmetically desirable smooth, soft and moisturized feel.

SUMMARY OF THE INVENTION

The present invention relates to a shampoo or body wash composition that can be used to both clean and condition the skin or hair. The composition contains from about 1 weight percent to about 40 weight percent, based on the total weight of the composition of at least one anionic surfactant; a conditioning complex, and at least about 40 weight percent of water. The conditioning complex is formed from at least (i) about 0.01 weight percent to about 4 weight percent, based on the total weight of the composition, of at least one alkyl amidoamine where at least one of the substituents of the tertiary amine is $R_1CONHR_2$—, where $R_1$ is an alkyl group having from about 9 to about 21 carbon atoms, and $R_2$ is an alkylene group having from 1 to about 8 carbon atoms; and (ii) at least one phosphate ester having a formula II

where $R_6$ is an alkylene group having from about 2 to about 4 carbon atoms, $R_7$ is an alkyl group having from about 8 to about 22 carbon atoms, n is a number ranging from 1 to about 30, $R_8$ is hydrogen, an $R_7(OR_6)_n$— group, an alkyl group having from 1 to about 5 carbon atoms, a hydroxyalkyl group having from 1 to about 5 carbon atoms, an alkali metal, alkaline earth metal, diethanolamine, or ammonium group, and where the amount of phosphate ester added to the composition is such that a solution consisting of water, the alkyl amidoamine in the amount used in the shampoo or body wash composition, and the phosphate ester in the amount used in the shampoo or body wash composition, results in an aqueous pH ranging from about 4 to about 6. The composition has a pH of from about 4 to about 6.

The present invention also provides a method of treating skin or hair comprising contacting the skin or hair with the composition of the present invention.

The present invention is also directed to a water-dispersible conditioning complex formed by the steps that include combining the alkyl amidoamine of (i) and the phosphate ester of (ii) to form a mixture, where the molar ratio of the phosphate ester to the alkyl amidoamine ranges from about (1:1) to about (3:1).

DETAILED DESCRIPTION OF THE INVENTION

The shampoo or body wash composition of the present invention cleans the skin and/or hair, while also having conditioning properties. By "shampoo or body wash composition" it is meant any composition useful for cleaning the skin and/or hair. By "cleaning" it is meant removing substances such as dirt and sebum from hair and/or skin. By "conditioning" it is meant that skin treated with the composition is preferably smooth, moisturized, and/or soft, and hair treated with the composition is preferably soft, smooth, and/or free of tangles.

The composition of the present invention contains a special conditioning complex and an anionic surfactant. The conditioning complex surprisingly enhances the quantity and/or quality of foam produced by the anionic surfactant, while also providing conditioning benefit to the skin or hair. Other benefits of the composition of the present invention include reduced irritation due to excessive defatting of the skin and scalp. The composition may also, if desired, be formulated as a transparent formulation, semi-transparent, or opaque formulation.

The conditioning complex of the present invention is preferably water dispersible and is formed from at least a tertiary alkyl amidoamine and a phosphate ester. By "water-dispersible" it is meant that the conditioning complex is dispersible in the shampoo or body wash composition of the present invention, but preferably not dissolved in water. By "formed from at least", it is meant that at least the alkyl amidoamine and the phosphate ester are combined to form the conditioning complex. One skilled in the art will recognize that it is possible that other optional compounds such as water are present when the conditioning complex is formed.

Although not intending to be bound by theory, tertiary alkyl amidoamines are strongly alkaline materials that are generally neutralized with acids to form cationic conditioning compounds useful in rinse-off hair conditioners. For example, when tertiary alkyl amidoamines are neutralized with water-soluble acids, such as citric acid, the alkyl amidoamine becomes a water-soluble cationic quaternary conditioner. These conditioners although having good substantivity to the hair or skin, are not deposited on the hair and skin in a sufficient amount, resulting in a feeling of softness, but no perceptible emollience (i.e., smoothness). When the tertiary alkyl amidoamine is neutralized with a high molecular weight fatty acid, such as stearic acid, the alkyl amidoamine becomes an oil-soluble cationic quaternary emulsifier, having good substantivity to the skin or hair, but very poor rinseability. This results in the hair feeling heavy and/or greasy and the skin feeling greasy and or coated after treatment with this compound. The present inventors have discovered that certain phosphate esters can be used to neutralize tertiary alkyl amidoamines to form a cationic conditioning complex that has good substantivity to hair and skin, can be deposited on the hair and skin in an adequate amount, and can also be adequately rinsed from the skin or hair, leaving hair soft and manageable and skin smooth and moisturized.

The conditioning complex of the present invention is compatible with anionic surfactants typically used in shampoo or body wash compositions. Additionally, it has unexpectedly been discovered that while most cationic conditioning compounds adversely effect the foaming properties of anionic surfactants, the conditioning complex of the present invention actually enhances the foam volume and foam quality (e.g., creaminess) of the anionic surfactant.

Tertiary alkyl amidoamines useful in the present invention are tertiary amines where at least one of the substituents of the amine is $R_1CONHR_2$—, where $R_1$ is an alkyl group having from about 9 to about 21 carbon atoms, and $R_2$ is an alkylene group having from 1 to about 8 carbon atoms. The tertiary alkyl amidoamine is preferably water dispersible.

The alkyl amidoamine used to form the conditioning complex is preferably in an amount to provide some conditioning benefit to the skin or hair. Preferably, the amount of alkyl amidoamine used to form the conditioning complex is at least about 0.01 weight percent, more preferably from about 0.1 weight percent to about 4 weight percent, and most preferably from about 0.2 weight percent to about 1 weight percent, based on the total weight of the shampoo or body wash composition.

Preferred tertiary alkyl amidoamines include those of the following formula I:

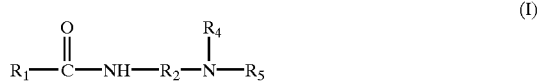

where $R_1$ is an alkyl group having from about 9 to about 21 carbon atoms, $R_2$ is an alkylene group having from 1 to about 8 carbon atoms, and $R_4$ and $R_5$ are independently an alkyl group having 1 to about 5 carbon atoms, or a hydroxyalkyl group having from 1 to about 5 carbon atoms. The alkyl groups and/or alkylene groups of $R_1$ to $R_5$, as chemically possible, may be linear, branched, saturated, or unsaturated or combinations thereof. One skilled in the art will also recognize that the $R_1$ does not have to be solely or primarily of one chain length such as lauryl ($C_{12}$) or stearyl ($C_{18}$). Rather, $R_1$ may be a mixture of chain lengths. Such alkyl amidoamine compounds may be conveniently prepared from naturally occurring materials such as tallow, coconut oil, soya oil, or combinations thereof, or from synthetically produced mixtures.

In a preferred embodiment of the present invention, $R_1$ is an alkyl group having from about 12 to about 20 carbon atoms and more preferably from about 14 to about 18 carbon atoms, $R_2$ is an alkylene group having from about 2 to about 4 carbon atoms, and more preferably from about 2 to about 3 carbon atoms, and $R_4$ and $R_5$ are independently methyl, ethyl, propyl, or combinations thereof.

Specific examples of alkyl amidoamines useful in the present invention include lauramidopropyldimethylamine, stearamidopropyldimethylamine, isostearamidopropyldimethylamine, stearamidopropyldiethanolamine, stearamidoethyldiethanolamine, stearamidoethyldiethylamine, cocamidopropyldimethylamine, wheat germ-amidopropyldimethylamine, palmitamidopropyldimethylamine, soyamidopropyldimethylamine, myristamidopropyldimethylamine, oleamidopropyldimethylamine, ricinoleamidopropyl dimethylamine, or combinations thereof. Preferably, the tertiary alkyl amidoamine is isostearamidopropyl dimethylamine, oleamidopropyldimethylamine, ricinoleamidopropyl dimethylamine, or combinations thereof.

The above alkyl amidoamines are commercially available for example as LEXAMINE 0-13 or LEXAMINE S-13 supplied by Inolex Chemical Div., Philadelphia, Pa. and as MACKINE 201 or MACKINE 401 supplied by McIntyre Group Ltd.

The phosphate ester of the present invention is a phosphate ester of an alkoxylated ether of a fatty alcohol where the fatty alcohol has from about 8 to about 22 carbon atoms and the alkoxylated ether preferably has from 1 to about 30 alkoxy groups, where the alkoxy groups have from about 2 to about 4 carbon atoms. The phosphate ester also has at least one acidic hydrogen for forming a complex with the alkyl amidoamine. Preferably, the phosphate ester includes at least one compound of formula II:

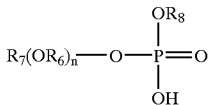

(II)

where $R_6$ is an alkylene group having from about 2 to about 4 carbon atoms, $R_7$ is an alkyl group having from about 8 to about 22 carbon atoms, n is a number ranging from 1 to about 30, $R_8$ is hydrogen, an $R_7(OR_6)_n$— group, an alkyl group having from 1 to about 5 carbon atoms, a hydroxy-alkyl group having from 1 to about 5 carbon atoms, an alkali metal, alkaline earth metal, diethanolamine, or ammonium group. The alkyl groups and/or hydroxyalkyl groups of $R_7$ to $R_8$, as chemically possible, may be linear, branched, saturated, or unsaturated or combinations thereof. One skilled in the art will also recognize that the carbon portion of the ($OR_6$) group may be linear or branched, and/or $R_7$ of formula II may be a mixture of chain lengths, such as described in connection with $R_1$ of formula I.

In a preferred embodiment of the present invention, $(OR_6)$ is a $C_2$ to $C_3$ alkoxy group and more preferably a mixture of ethoxy and propoxy groups where the number of ethoxy groups ranges on average from about 5 to about 15, and more preferably from about 7 to about 11, and the number of propoxy groups ranges on average from about 1 to about 10 and more preferably from about 3 to about 6, $R_7$ is an alkyl group having from about 12 to about 20 carbon atoms and more preferably from about 14 to about 18 carbon atoms, n is a number ranging from about 5 to about 25 and more preferably from about 10 to about 20, $R_8$ is hydrogen, or an $R_7(OR_6)_n$— group, or combinations thereof.

In a most preferred embodiment of the present invention, the phosphate ester is a mixture of monoester, where $R_8$ is hydrogen, and a diester where $R_8$ is a $R_7(OR_6)_n$— group. Preferably the weight ratio of monoester to diester is from about (1:10) to about (10:1) and more preferably from about (1:2) to about (2:1). Preferably also $(OR_6)_n$ is a mixture of ethoxy and propoxy groups where the average number of ethoxy groups is from about 7 to about 12 and the average number of propoxy groups is from about 2 to about 6 for each $R_7(OR_6)_n$— group. Also preferably, $R_7$ is an alkyl group having from about 14 to 18 carbon atoms or mixtures thereof.

An example of a most preferred phosphate ester useful in the present invention is an alkoxylated ether of cetyl alcohol having on average 5 propoxy groups and 10 ethoxy groups. Such a phosphate ester is known as PPG-5-Ceteth-10 Phosphate and is commercially available from such suppliers as Croda, Inc. located in New Jersey under the name Crodafos SG.

PPG-5-Ceteth-10 Phosphate is a mixture of the phosphate monoester and diester of propoxylated ethoxylated ether of cetyl alcohol, and has the general formulae:

Monoester

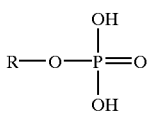

-continued

Diester

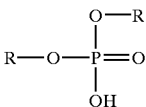

where R represents:

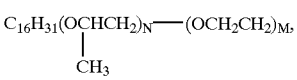

N averages 5, and M averages 10.

Other commercial phosphate esters are available under the trade names of Monafax 831 or 1214, supplied by Mona.

The amount of phosphate ester used to form the conditioning complex is preferably in an amount that a solution containing just water, the alkyl amidoamine in the amount used in the shampoo or body wash composition, and the phosphate ester results in an aqueous pH that is about the pH of healthy skin and hair. Preferably this pH ranges from about 4 to about 6, more preferably from about 4.5 to about 5.5 and most preferably about 5. Although the amount of phosphate ester needed to achieve this pH will depend on the number of acidic hydrogens on the phosphate ester, generally the ratio of moles of phosphate ester to the moles of alkyl amidoamine used to form the conditioning complex should preferably be from about (1:1) to about (3:1), and more preferably from about (1.5:1) to about (2:1). Thus, one skilled in the art would recognize that the moles of phosphate ester used to form the conditioning complex is preferably in an excess molar amount compared to the molar amount needed to neutralize the alkyl amidoamine. Accordingly, it is believed that not all the phosphate ester present in the shampoo or body wash composition complexes with the alkyl amidoamine in the conditioning complex.

Since the pH of the conditioning complex is preferably prepared to be about the pH of healthy skin and hair, the film deposited on the skin and hair by the shampoo or body wash composition produces a soft, moisturized, emollient feel on the skin or hair. The conditioning complex could also be used in conditioners.

The shampoo or body wash composition also contains at least one anionic surfactant. Any anionic surfactant may be used that is dermatologically compatible with skin or hair. By "dermatologically compatible" it is meant that the compound does not cause irritation when applied to the skin for the purpose of cleaning and then is subsequently removed within about 30 minutes of application. The anionic surfactant is preferably present at a level of from about 1 weight percent to about 40 weight percent, more preferably from about 5 weight percent to about 30 weight percent, and most preferably from about 5 weight percent to about weight percent, based on the total weight of the composition.

Anionic surfactants useful in the present invention are well known and include for example alkyl sulfates, alkyl ether sulfates, alkyl ether carboxylates, acyl isethionates, acyl sarcosinates, acyl taurines, or alkali metal, ammonium, or alkanolammonium salts thereof, or combinations thereof. Preferably, the alkyl or acyl groups of these surfactants contain from about 10 to about 20 carbon atoms per alkyl or acyl group, more preferably from about 12 to about 18 carbon atoms per alkyl or acyl group. The alkyl or acyl groups may be linear, branched, saturated or unsaturated or combinations thereof. More preferably, the alkyl or acyl groups are linear.

In a preferred embodiment of the present invention the anionic surfactant includes at least one alkyl sulfate, alkyl ether sulfate, salts thereof, or combinations thereof. These surfactants have respectively the general formulae:

$$R_9OSO_3^-M^+ \text{ and } R_9O(C_2H_4O)_xSO_3^-M^+$$

where $R_9$ is an alkyl group of about 10 to about 20 carbon atoms, more preferably about 12 to about 18 carbon atoms, x is 1 to about 10, more preferably 1 to about 4, and $M^+$ is a water-soluble cation such as ammonium, an alkali metal salt such as sodium or potassium, or an alkanolammonium salt such as triethanolamine.

Specific examples of preferred anionic surfactants useful in the present invention include ammonium lauryl sulfate, sodium lauryl sulfate, ammonium laureth sulfate (preferably with 1 to about 3 moles ethylene oxide), sodium laureth sulfate (with preferably 1 to about 3 moles ethylene oxide), or combinations thereof.

The conditioning complex and anionic surfactant are formulated with water as a carrier to form the shampoo or body wash conditioning composition of the present invention. Water is preferably present in an amount of at least about 40 weight percent, more preferably from about 50 weight percent to about 90 weight percent, and most preferably from about 60 weight percent to about 80 weight percent, based on the total weight of the composition.

In addition to water the composition may also contain other carriers such as organic solvents. Such organic solvents, if at all present, should be present in the composition in an amount of no more than about 5 weight percent and more preferably in an amount of from about 0.1 to about 1 weight percent. Examples of organic solvents include $C_2$ to $C_6$ monoalcohols, such as ethanol, propanol, isopropanol, or tert-butyl alcohol; ethylene glycol; ethylene glycol monomethyl ether; ethylene glycol monoethyl ether; ethylene glycol monobutyl ether; ethylene glycol monoethyl ether acetate; propylene glycol; propylene glycol monomethyl ether; dipropylene glycol monomethyl ether; glycerol; or diethylene glycol; or combinations thereof. Preferably, the shampoo or body wash composition of the present invention is formulated as a monoalcohol-free composition.

The shampoo or body wash composition of the present invention is at a pH that is dermatologically compatible with skin and hair. Preferably, the pH of the shampoo or body wash composition is from about 4 to about 6, more preferably from about 4.5 to about 5.5, and most preferably about 5. If necessary, the pH of the shampoo or body wash composition may be adjusted with any of a number of commonly used cosmetic ingredients. Examples of suitable pH adjusters include acids for decreasing the pH including inorganic acids such as phosphoric acid, nitric acid, or hydrochloric acid, or organic acids such as citric acid or tartaric acid; or basic compounds for increasing the pH, including organic amines such as triethanolamine, ethanolamine, or aminomethylpropanol, alkali metal or alkaline earth metal hydroxides such as sodium hydroxide or potassium hydroxide; ammonium hydroxide, basic amino acids such as arginine, sodium hydroxymethylglycinate, or combinations thereof. The pH of the shampoo or body wash composition should not be adjusted with either of the components of the conditioning complex, the alkyl amidoamine, or the phosphate ester, as this would alter the ratio of these two components.

In a preferred embodiment of the present invention, the shampoo or body wash composition contains an amphoteric surfactant, zwitterionic surfactant, or combinations thereof. Preferably, the total amount of amphoteric and zwitterionic surfactant is from 0 to about 5 weight percent and more preferably from about 1 to about 4, based on the total weight of the composition.

Examples of suitable amphoteric or zwitterionic surfactants for use in the present invention include alkyl betaines, alkylamidobetaines, aminopropionates, aminoglycinates, imidazolinium betaines, sulfobetaines or combinations thereof.

A preferred zwitterionic surfactant of the present invention includes compounds having formula III:

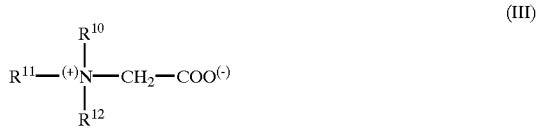
(III)

where $R^{11}$ is an alkyl or alkenyl group containing from about 10 to about 20 carbon atoms or a $R^{13}$—$CONH$—$(CH_2)_p$ group, where $R^{13}$ is an alkyl or alkenyl group containing from about 10 to about 20 carbon atoms and p is a number of from about 2 to about 5, and $R^{10}$ and $R^{12}$ are alkyl groups containing from 1 to about 5 carbon atoms or hydroxyalkyl groups containing from about 2 to about 4 carbon atoms.

Preferred amphoteric surfactants includes compounds having formula IV:

(IV)

where $R^{11}$ is an alkyl or alkenyl group containing from about 10 to about 20 carbon atoms or a $R^{13}$—$CONH$—$(CH_2)_p$ group, where $R^{13}$ is an alkyl or alkenyl group containing from about 10 to about 20 carbon atoms and p is a number of from about 2 to about 5, and $R^{14}$ is an alkyl group containing from 1 to about 5 carbon atoms or a hydroxyalkyl group containing from about 2 to about 4 carbon atoms.

Examples of amphoteric or zwitterionic surfactants useful in the present invention include sodium 3-dodecyl-aminopropionate, sodium 3-dodecylaminopropane sulfonate, sodium lauroamphoacetate, coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, oleamidopropyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine or combinations thereof. Most preferably, the zwitterionic or amphoteric surfactant is cocoamidopropyl betaine, oleamidopropyl betaine, or combinations thereof.

In addition to the above-described components, other common cosmetic additives may be included in the composition of the present invention, as long as the basic properties of the shampoo or body wash composition are not adversely affected. Such optional cosmetic additives may be found, for example, in the International Cosmetic Ingredients Dictionary, 7th Edition, 1997, published by the CTFA in Washington D.C. Preferably, these optional components, in total, are present in an amount of from 0 to 20 weight percent, and more preferably from about 0.1 to about 12 weight percent, based on the total weight of the composition.

Examples of optional additive components include, but are not limited to, one or more surfactants such as nonionic surfactants or cationic surfactants, protein hydrolyzates, other conditioning agents, inorganic electrolyte salts or combinations thereof.

Other types of surfactants, not previously described herein, that are typically used in shampoo or body wash compositions may optionally be added to the composition of the present invention such as nonionic and/or cationic surfactants. Preferably, these surfactants are present in an amount of no more than about 10 weight percent, more preferably in an amount of 0 weight percent to about 5 weight percent, and most preferably in an amount of about 0.01 weight percent to about 3 weight percent, based on the total weight of the composition. Surfactants may include for example, nonionic surfactants present in an amount preferably ranging from 0 weight percent to about 10 weight percent and more preferably from 0 weight percent to about 2 weight percent, based on the total weight of the composition. Examples of nonionic surfactants include for example alkyl polyglycosides, alkyl oligoglycosides, ethoxylated fatty alcohols, sorbitan esters, or alkanolamides such as cocamide MEA, cocamide DEA, soyamide DEA, lauramide DEA, lauramide MEA, lauramide MIPA, oleamide MIPA, ricinoleamide DEA, stearamide MEA, stearamide DEA, isostearamide MEA, isostearamide DEA, myristamide MEA, lauramide MEA, capramide DEA, stearamide DEA, oleylamide DEA, myristamide DEA, or tallowamide DEA, or combinations thereof. Surfactants may also be cationic surfactants present in an amount preferably ranging from 0 weight percent to about 5 weight percent and more preferably from 0 weight percent to about 1 weight percent, based on the total weight of the composition. Examples of cationic surfactants include quaternary ammonium compounds. A more extensive list of surfactants are described for example in U.S. Pat. No. 5,955,066, and McCutcheon's Emulsifiers & Detergents, North American Edition and International Edition, 1999 Annuals, published by McCutcheon's Division, MC Publishing Company, Glen Rock, N.J. (1999). The complete disclosure of these documents are incorporated herein by reference in their entireties.

Protein hydrolyzates may also be present in the composition in an amount of up to about 2.0 weight percent, based on the total weight of the composition. Examples of protein hydrolyzates include elastin, collagen, keratin, milk protein, soya protein, or wheat protein hydrolyzates, or condensation products thereof with fatty acids, or quaternized protein hydrolyzates, or combinations thereof.

Examples of other conditioning agents suitable for use in the present invention include compounds that soften, strengthen, add shine and/or detangle the hair, or soften and/or moisturize skin, such as phospholipids (e.g., soya lecithin, egg lecithin or kephalins), silicone compounds, proteins, amino acids, or combinations thereof. Suitable silicone compounds include, for example, polyalkylsiloxanes, polyarylsiloxanes, polyarylalkylsiloxanes, polyethersiloxanes or silicone resins. Preferably, these conditioning agents are present in the composition in an amount of no more than about 1 weight percent, more preferably from 0 weight percent to about 0.75 weight percent and most preferably from 0 weight percent to about 0.1 weight percent, based on the total weight of the composition.

Inorganic electrolyte salts may also be added to the composition of the present invention in an amount of from 0 weight percent to about 2 weight percent, based on the total weight of the composition. Such electrolyte salts may be added, for example, to thicken the composition. Inorganic electrolyte salts that may be used are any water-soluble alkali metal, ammonium or alkaline earth metal salt, for example the fluorides, chlorides, bromides, sulfates, phosphates, nitrates or hydrogen carbonates, providing that they are soluble in water at 20° C. in a quantity of at least 1 percent by weight. Sodium chloride and magnesium chloride are especially preferred.

The shampoo or body wash composition of the present invention may also contain as optional additive components, one or more sequestrants such as ethylene diamine tetraacetic acid (EDTA), or phosphonic acids; fragrances; other nonactive ingredients such as panthenol, allantoin, pyrrolidone carboxylic acids or salts thereof; plant extracts; vitamins such as Vitamins A, B, C, or E, or combinations thereof; preservatives such methylchloroisothiazolinone, methylisothiazolinone, or diazolidinyl urea or combinations thereof; humectants, such as sorbitol, glycerin, propylene glycol, or butylene glycol or combinations thereof; light stabilizers; dyes; pearlescers, such as ethylene glycol monostearate or distearate; antioxidants; thickeners such as polysaccharides, including for example, xanthan gum, guar gum, agar gum, alginates, tyloses, or celluloses such as carboxymethyl cellulose, or hydroxyethyl cellulose; polyethylene glycol monoesters or diesters of fatty acids having a molecular weight of at least about 200,000; poly(meth) acrylic acid or salts thereof; polyvinyl alcohol; or fatty alcohol ethoxylates; or any combination of any of the foregoing additives. The selection of these optional additives will depend upon the composition that is desired to be formulated. Preferably, these optional additives are present individually in the composition in an amount of no more than about 1 weight percent and more preferably in an amount of no more than about 0.5 weight percent.

In another embodiment of the present invention, a method is provided for treating skin or hair using the composition of the present invention. The composition is preferably applied to skin or hair that has first been wetted with water. Following application of the composition to skin or hair, the composition is preferably rinsed from the skin or hair with water to remove any undesirable substances such as dirt or sebum. The composition has the advantage of both simultaneously cleaning and conditioning the skin or hair.

The composition of the present invention is preferably prepared by adding the anionic surfactant to water and adjusting the pH to about 4 to about 6. Following adjustment of the pH, the alkyl amidoamine and phosphate ester are added to the surfactant solution with mixing. One skilled in the art will recognize that if the amidoamine or phosphate ester are solids at room temperature, they may be warmed until melted and added in melted form to the surfactant solution. One skilled in the art will also recognize that there are various other ways to prepare the composition of the present invention.

EXAMPLES

To demonstrate the effectiveness of the shampoo or body wash composition of the present invention, the following Examples were prepared. The weight percentage listed in each of the following examples represents the amount of each ingredient present in the shampoo or body wash composition. The compositions were prepared by combining the ingredients in the order of appearance in Table 1 below, except that in Ex.2, the stearic acid was melted and mixed with the amidoamine prior to being added to the surfactant solution:

TABLE 1

Compositions Evaluated

| Ingredients | Ex. 1 (comp) | Ex. 2 (comp) | Ex. 3 | Ex. 4 | Ex. 5 |
|---|---|---|---|---|---|
| Water | qs to 100 | qs to 100 | qs to 100 | qs to 100 | qs to 100 |
| Sodium Laureth-2 Sulfate 27 wt % active | 30 | 30 | 30 | 20 | 20 |
| Cocamidopropyl Betaine 30 wt % active | 0 | 0 | 0 | 8 | 0 |
| Oleamidopropyl Betaine | 0 | 0 | 0 | 0 | 8 |
| Methylchloroisothiazolinone Methylisothiazolinone | 0.08 | 0.08 | 0.08 | 0.08 | 0.08 |
| Citric Acid | qs pH 5 | qs pH 5 | qs pH 5 | qs pH 5 | qs pH 5 |
| PPG-5-Ceteth-10-Phosphate[1] | 0 | 0 | 0.70 | 0.68 | 0.70 |
| Stearic Acid | 0 | 0.4 | 0 | 0 | 0 |
| Isostearamidopropyl Dimethylamine[2] | 0.30 | 0.30 | 0.30 | 0 | 0 |
| Rocinoleamidopropyl Dimethylamine[3] | 0 | 0 | 0 | 0.32 | 0 |
| Oleamidopropyl Dimethylamine[4] | 0 | 0 | 0 | 0 | 0.30 |
| Sodium Chloride | 1.20 | 1.20 | 1.20 | 1.00 | 1.00 |

[1]Crodafos SG, supplied by Croda, Inc.
[2]Mackine 401, supplied by McIntyre.
[3]Mackine 201, supplied by McIntyre
[4]Lexamine 0–13, supplied by Inolex.

The compositions of Examples 3 to 5 (compositions of the present invention) are transparent liquids having a pH of about 5.0 and a viscosity of about 5,000 to about 10,000 centipoise. The compositions of Examples 3 to 5 exhibited excellent storage stability, showing no phase separation or ingredient precipitation after storage for several weeks at about 4° C., about 25° C., and about 45° C. The compositions of Examples 1 to 5 were further evaluated as shown below:

TABLE 2

Properties of Examples 1 to 5

| Property | Ex. 1 (comp.) | Ex. 2 (comp.) | Ex. 3 | Ex. 4 | Ex. 5 |
|---|---|---|---|---|---|
| Appearance (visual) | Clear | Opaque | Clear | Clear | Clear |
| Foam quantity | Good | Poor | Excellent | Excellent | Excellent |
| Conditioning benefit to skin and hair | Good | Poor (waxy/greasy) | Excellent | Excellent | Excellent |

The foam quantity and conditioning benefit in the table above was evaluated by applying the composition to wetted skin and hair and subsequently rinsing the composition with water. The foam quantity and conditioning benefit was qualitatively ranked as either excellent, good, or poor. As can be seen from the results above, the composition of the present invention (Examples 3 to 5) produced more foam and more conditioning benefit in comparison to compositions of comparative Examples 1 and 2, where the alkyl amidoamine was neutralized with citric acid and stearic acid, respectively.

Although the present invention has been described above with respect to particular preferred embodiments, it will be apparent to those skilled in the art that numerous modifications and variations can be made to the present invention without departing from the scope of the present invention.

What is claimed is:
1. A shampoo or body wash composition comprising:
(a) from about 1 weight percent to about 40 weight percent, based on the total weight of the composition of at least one anionic surfactant;
(b) a water-dispersible conditioning complex, which does not dissolve in water, formed from at least
(i) about 0.01 weight percent to about 4 weight percent, based on the total weight of the composition, of at least one tertiary alkyl ammidoamine, wherein at least one of the substituents of the tertiary amine is R1CONHR2—, wherein R1 is an alkyl group having from about 9 to about 21 carbon atoms, and R2 is an alkylene group having from 1 to about 8 carbon atoms; and
(ii) at least one phosphate ester having a formula II

wherein R6 is an alkylene group having from about 2 to about 4 carbon atoms, R7 is an alkyl group having from about 8 to 22 carbon atoms, n is a number ranging from 1 to about 30, R8 is hydrogen, an R7(OR6)n— group, an alkyl group having from 1 to about 5 carbon atoms, a hydroxyalkyl group having from 1 to about 5 carbon atoms, an alkali metal, alkaline earth metal, diethanolamiine, or ammonium group, and wherein the amount of phosphate ester added to the composition is such that a solution consisting of water, the alkylamidoamine in the amount used in the shampoo or body wash composition, and the phosphate ester in the amount used in the shampoo or body wash composition, results in an aqueous pH ranging from about 4 to about 6, and wherein the molar ratio of the phosphate ester to the tertiary alkyl amidoamine is from about (1:1) to about (3:1) wherein the moles of phosphate ester used to form the conditioning complex is in an excess molar amount compared to the molar amount needed to neutralize the alkyl amidoamine; and (c) at least about 40 weight percent of water, wherein the composition has a pH of from about 4.0 to about 6.0.

2. The composition of claim 1 wherein the tertiary alkyl amidoamine has a formula I:

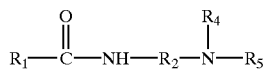
(I)

wherein $R_1$ and $R_2$ have the same meaning as in claim 1, and $R_4$ and $R_5$ are independently an alkyl group having 1 to about 5 carbon atoms, or a hydroxyalkyl group having from 1 to about 5 carbon atoms.

3. The composition of claim 2 wherein the $R_1$ is an alkyl group having from about 12 to about 20 carbon atoms, $R_2$ is an alkylene group having from about 2 to about 3 carbon atoms, and $R_4$ and $R_5$ are independently methyl, ethyl, or propyl.

4. The composition of claim 3 wherein the tertiary alkylamidoamine comprises oleamidopropyl dimethylamine, ricinoleamidopropyl dimethylamine, isostearamidopropyl dimethylamine, or mixtures thereof.

5. The composition of claim 1 wherein the phosphate ester is a mixture of monoester and diester, wherein $(OR6)$ is a C2 to C3 alkoxy group or mixtures thereof, R7 is an alkyl group having from about 12 to about 20 carbon atoms, n is a number ranging from about 5 to about 25, and R8 is hydrogen, or an $R7(OR6)n$— group.

6. The composition of claim 5 wherein the phosphate ester is PPG-5 Ceteth-10 Phosphate.

7. The composition of claim 5 wherein the anionic surfactant comprises sodium lauryl sulfate, sodium laureth sulfate, ammonium lauryl sulfate, ammonium laureth sulfate, or mixtures thereof.

8. The composition of claim 7 further comprising a nonionic surfactant.

9. The composition of claim 7 further comprising an amphoteric surfactant, a zwitterionic surfactant, or combinations thereof.

10. A shampoo or body wash composition comprising:

(a) from about 1 weight percent to about 40 weight percent, based on the total weight of the composition of at least one anionic surfactant;

(b) a water-disposable conditioning complex, which does not dissolve in water, formed from at least (i) about 0.01 weight percent to about 4 weight percent, based on the total weight of the composition, of at least one tertiary alkyl amidoamine, wherein the tertiary alkyl amidoamine has a formula I:

(I)

wherein $R_1$ is an alkyl group having from about 9 to about 21 carbon atoms, $R_2$ is a linear, saturated alkylene group having from about 1 to about 3 carbon atoms, $R_4$ and $R_5$ are independently methyl or ethyl; and (ii) at least one phosphate ester having a formula II

(II)

wherein $(OR_6)$ is a mixture of ethoxy and propoxy groups, $R_7$ is an alkyl group having about 16 carbon atoms, n is a number averaging about 15, $R_8$ is hydrogen, or an $R_7(OR_6)_n$— group, and wherein the amount of phosphate ester added to the composition is such that a solution consisting of water, the alkylamidoarmine in the amount used in the shampoo or body wash composition, and the phosphate ester in the amount used in the shampoo or body wash composition, results in an aqueous pH ranging from about 4.5 to about 5.5 and wherein the molar ratio of the phosphate ester to the tertiary alkyl amidoamine is from about (1:1) to about (3:1) wherein the moles of phosphate ester used to form the conditioning complex is in an excess molar amount compared to the molar amount needed to neutralize the alkyl amidoamine; and (c) at least about 40 weight percent of water, wherein the composition has a pH of from about 4.5 to about 5.5.

11. A water dispersible conditioning complex, which does not dissolve in water, formed by a process comprising combining (i) at least one alkylamidoamine having a formula I:

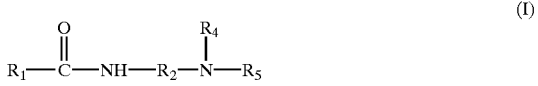
(I)

wherein $R_1$ is an alkyl group having from about 9 to about 21 carbon atoms, $R_2$ is an alkylene group having from 1 to about 8 carbon atoms, and $R_1$ and $R_5$ are independently an alkyl group having 1 to about 5 carbon atoms, or a hydroxyalkyl group having from 1 to about 5 carbon atoms; and (ii) at least one phosphate ester having a formula II

(II)

wherein $R_6$ is an alkylene group having from about 2 to about 4 carbon atoms, $R_7$ is an alkyl group having from about 8 to about 22 carbon atoms, n is a number ranging from 1 to about 30, $R_8$ is hydrogen, an $R_7(OR_6)$— group, an alkyl group having from 1 to about 5 carbon atoms, a hydroxyalkyl group having from 1 to about 5 carbon atoms, an alkali metal, an alkaline earth metal, diethanolamine, or ammonium group, and wherein the molar ratio of the phosphate ester to the alkyl amidoamine ranges from about (1:1) to about (3:1) wherein the moles of phosphate ester used to form the conditioning complex is in an excess molar amount compared to the molar amount needed to neutralize the alkyl amidoamine.

* * * * *

UNITED STATES PATENT AND TRADEMARK OFFICE
CERTIFICATE OF CORRECTION

PATENT NO. : 6,566,313 B1
DATED : May 20, 2003
INVENTOR(S) : Hohenstein et al.

It is certified that error appears in the above-identified patent and that said Letters Patent is hereby corrected as shown below:

Column 12,
Line 37, delete "ammidoamine" and insert therefore -- amidoamine --.
Line 54, delete "R7(OR$_6$)n" and insert therefore -- R7(OR6)n --.

Column 13,
Line 51, delete "water-disposable" and insert therefore -- water-dispersible --.

Column 14,
Line 15, delete "alkylamidoarmine" and insert therfore -- alkylamidoamine --.
Line 19, after "5.5", insert -- , --.
Line 41, delete "$R_1$" and insert therefore -- $R_4$ --.
Line 57, delete "$R_7(OR_6)$-" and insert therefore -- $R_7(OR_6)_n$- --.

Signed and Sealed this

Twelfth Day of October, 2004

JON W. DUDAS
*Director of the United States Patent and Trademark Office*